United States Patent [19]

Kaufman

[11] 4,307,731
[45] Dec. 29, 1981

[54] MULTIPLE SAMPLING NEEDLE HAVING ONE-WAY VALVE

[75] Inventor: Joseph Kaufman, Emerson, N.J.

[73] Assignee: Becton, Dickinson and Company, Paramus, N.J.

[21] Appl. No.: 107,738

[22] Filed: Dec. 27, 1979

Related U.S. Application Data

[63] Continuation-in-part of Ser. No. 915,671, Jun. 15, 1978, abandoned.

[51] Int. Cl.³ .................................................. A61B 5/14
[52] U.S. Cl. .................................... 128/766; 128/764; 137/854
[58] Field of Search .............................. 128/763–768, 128/274, 218 NV; 137/854; 73/425.4 P

[56] References Cited

U.S. PATENT DOCUMENTS

| | | | |
|---|---|---|---|
| 274,308 | 3/1883 | George | 137/854 X |
| 2,128,050 | 8/1938 | Landis | 137/854 |
| 2,663,540 | 12/1953 | Erikson | 137/854 X |
| 2,913,000 | 11/1959 | Roberts | 137/854 |
| 3,022,796 | 2/1962 | Cummings | 137/854 X |
| 3,331,390 | 7/1967 | Hoffman | 137/854 |
| 3,817,240 | 6/1974 | Ayres | 128/2 F |
| 3,848,579 | 11/1974 | Villa-Real | 128/2 F |
| 3,905,386 | 9/1975 | Rachocki | 137/854 |
| 3,949,780 | 4/1976 | Buckman | 137/854 |
| 4,106,497 | 8/1978 | Percarpio | 128/2 F |

FOREIGN PATENT DOCUMENTS

| | | | |
|---|---|---|---|
| 826926 | 1/1952 | Fed. Rep. of Germany | 137/854 |
| 2349996 | 2/1974 | Fed. Rep. of Germany | 128/DIG. 5 |
| 564936 | 7/1957 | Italy | 137/854 |
| 1199498 | 7/1970 | United Kingdom | 128/274 |

Primary Examiner—Kyle L. Howell

[57] ABSTRACT

A blood sampling device having a valve assembly which prevents the backflow of blood into a patient, and which is especially suitable for multiple sample collection. The valve assembly includes a mounting structure for a valve member, a chamber to house the valve, and a valve which has a resilient skirt allowing fluid flow only in one direction. The valve member is prevented from cocking by a protruding portion which fits within a recess of the mounting structure and by valve positioning members within the valve chamber.

22 Claims, 12 Drawing Figures

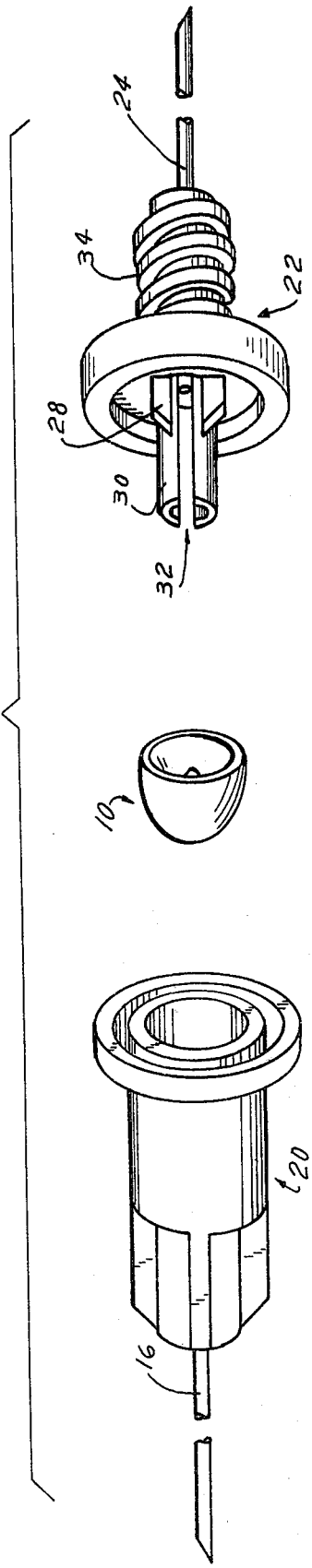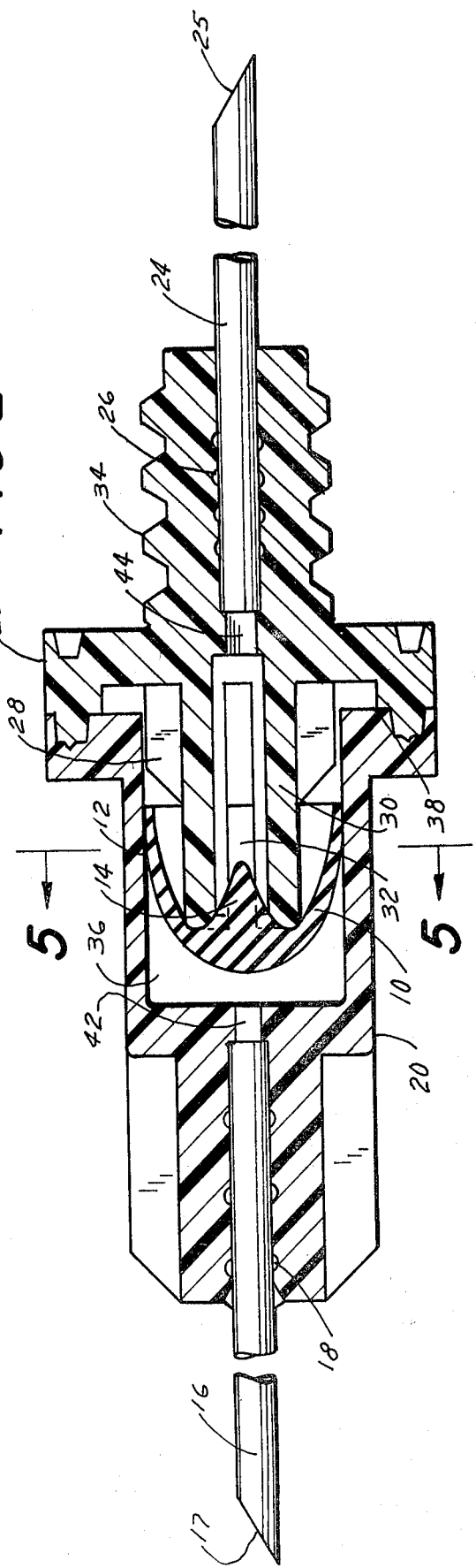

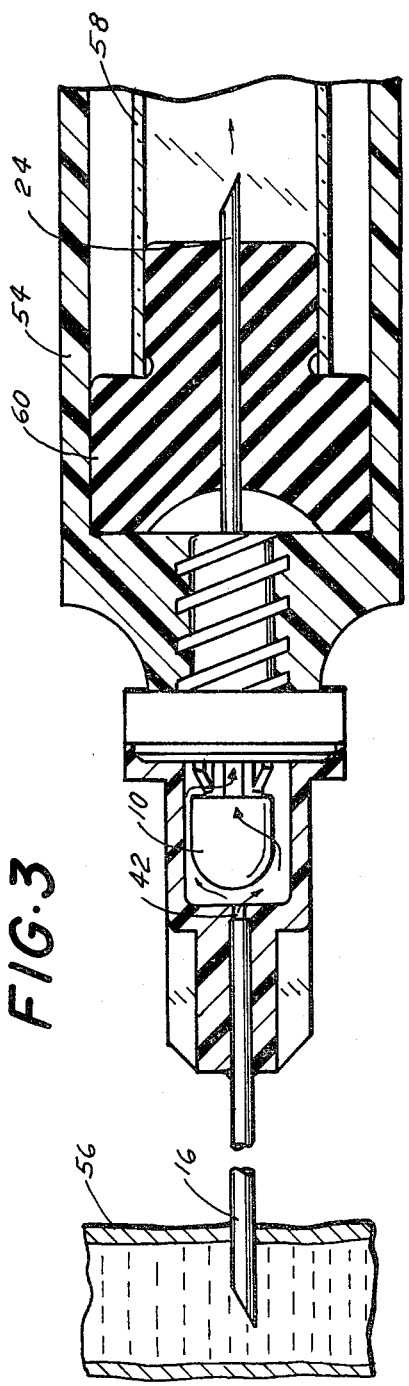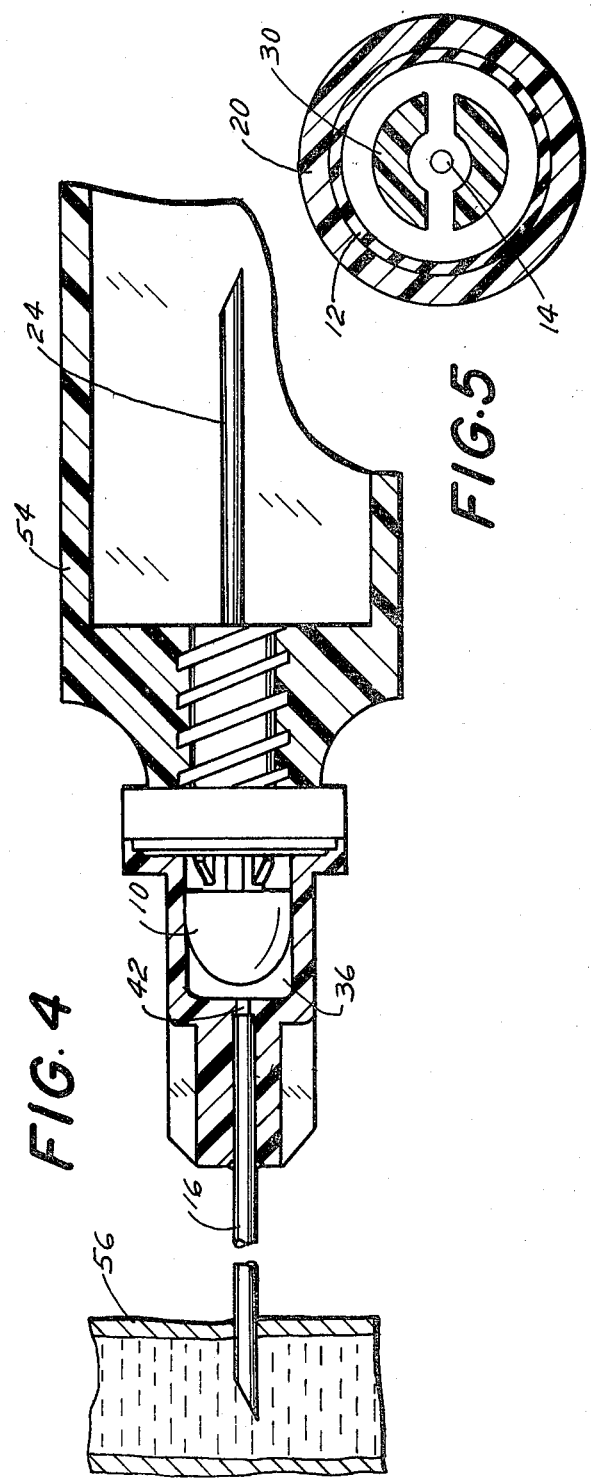

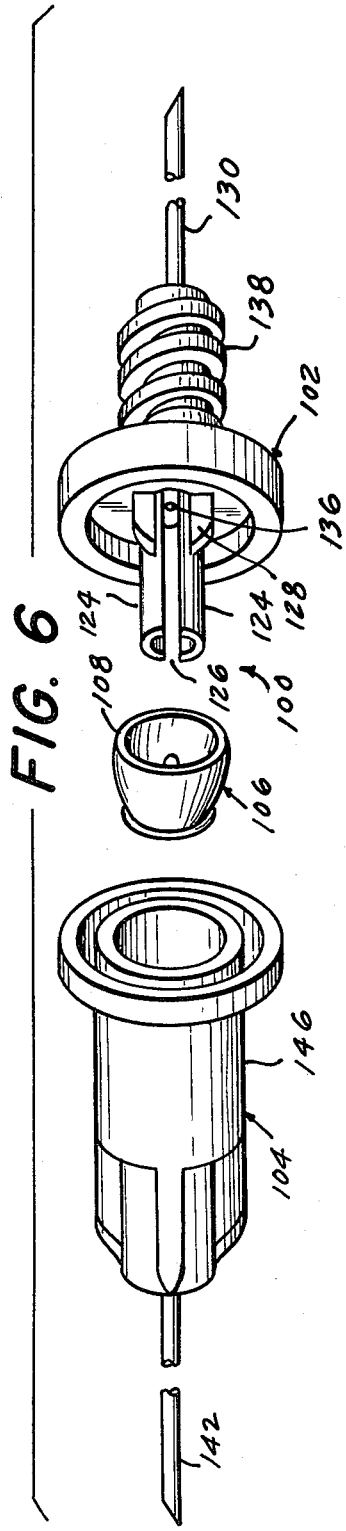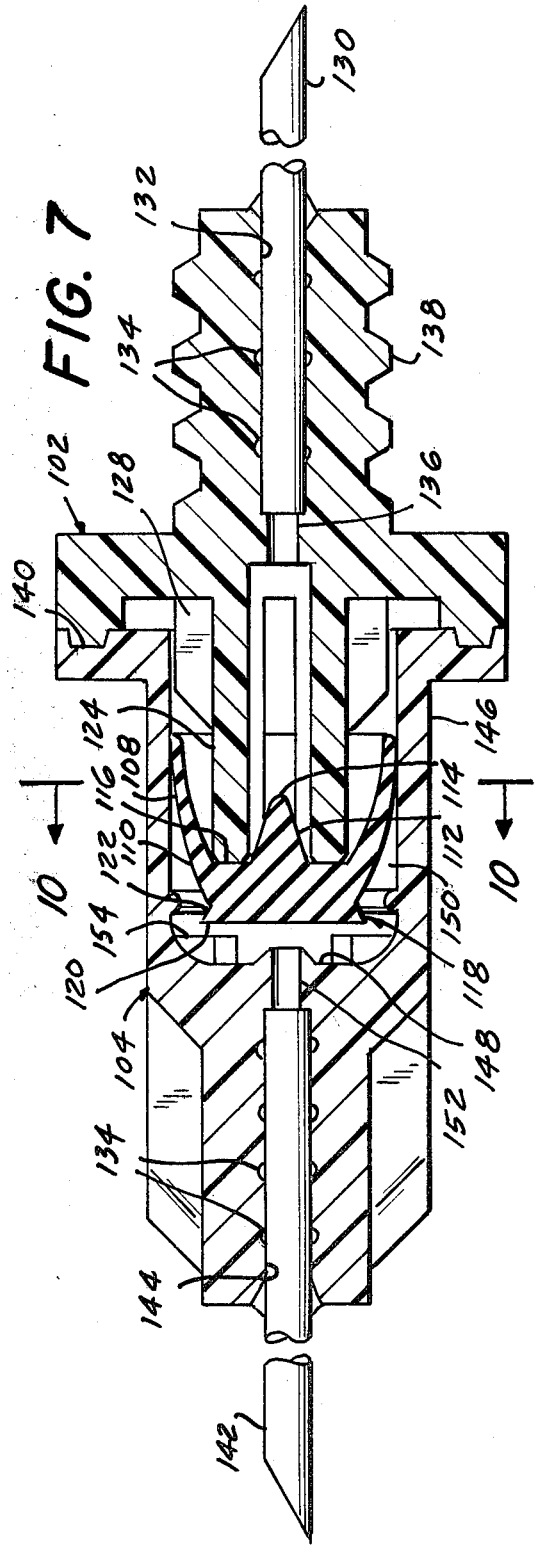

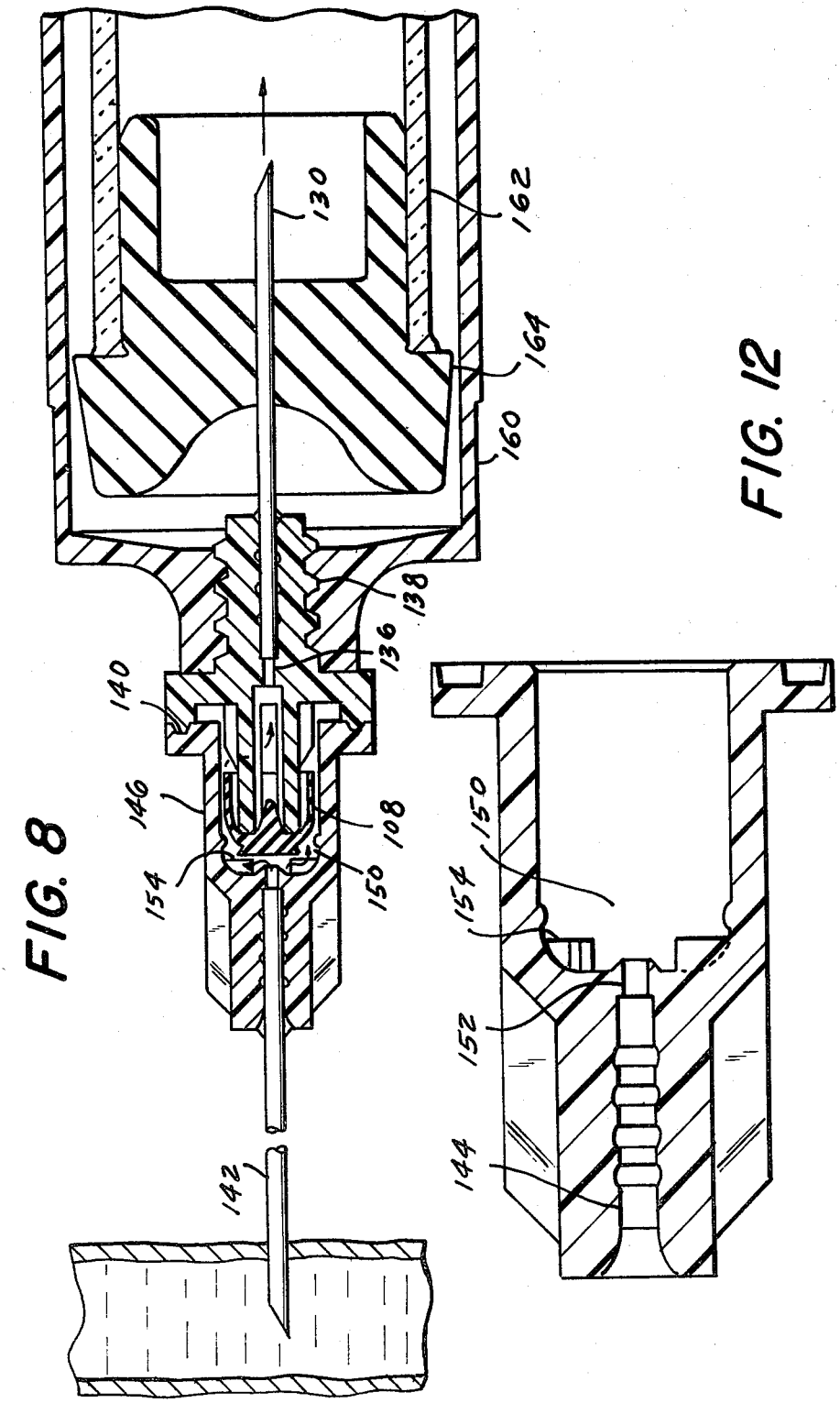

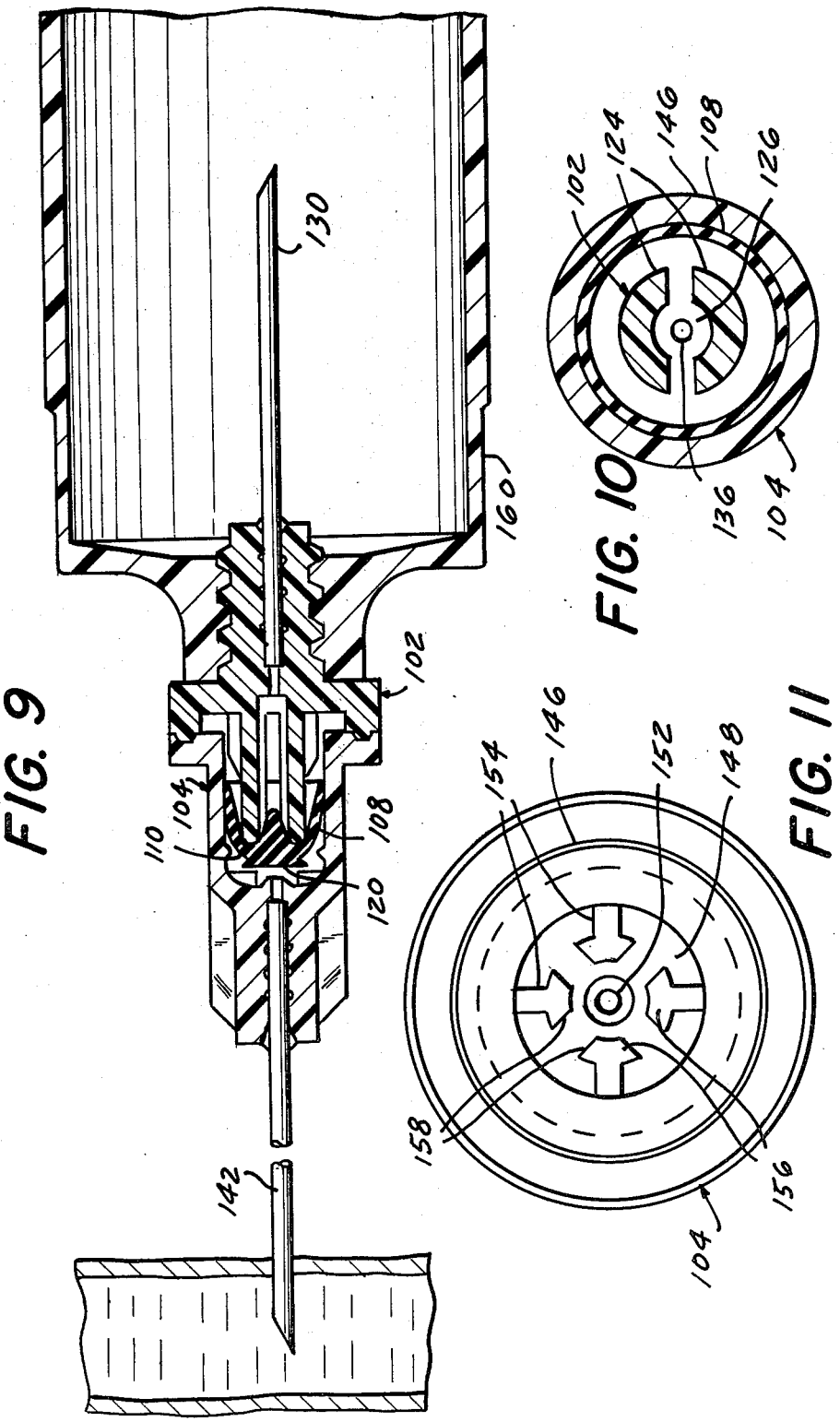

MULTIPLE SAMPLING NEEDLE HAVING ONE-WAY VALVE

CROSS REFERENCE TO RELATED APPLICATION

This application is a continuation-in-part of Ser. No. 915,671 filed June 15, 1978, now abandoned.

BACKGROUND OF THE INVENTION

The invention relates to the field of blood sampling devices, and particularly those adapted for multiple sample collection.

Various valve assemblies have been designed for controlling the direction of flow of fluids. These include, for example, ball and seat valves, duckbill valves, and cup-shaped or conical valves. The latter two valves operate by compressing or folding their elastomeric skirts under sufficient pressure, thereby permitting fluid to pass by in the forward direction. Pressure in the opposite direction tends to expand the flexible portion into sealing contact with the conduit walls. U.S. Pat. No. 2,913,000 discloses a cup-shaped flow control valve which operates in this manner.

Previous valve assemblies have not been applied to blood sampling devices in providing a simple structure for preventing backflow and allowing multiple sampling.

Prior multiple sampling assemblies also fail to disclose means to prevent cocking and malfunction of the valve.

Other blood sampling devices known to the art have features which enable their use as both check valves (preventing backflow) and multiple sampling device (preventing forward flow under tourniquet pressure). The latter feature enables the user to exchange evacuated blood collection tubes without leakage occuring due to venous or tourniquet pressure. The use of a simple, inexpensive cup valve in conjunction with an assembly specifically adapted to utilize its advantageous features has not previously been disclosed.

SUMMARY OF THE INVENTION

It is among the primary objectives of the invention to provide a blood sampling assembly with a valve member having a resilient skirt which has both multiple sampling features and the capability of acting as a check valve.

It is another object of the invention to provide a valve member with means to prevent cocking, thereby avoiding failure of the device.

Still another object of the invention is to provide a blood sampling assembly which is economical to manufacture.

To accomplish the above objectives, a valve assembly is provided with a valve member having a resilient skirt which will collapse under sufficient pressure in one direction of flow, but which will expand against the walls of a fluid conduit in which it is positioned to prevent flow in the opposite direction. The valve member has a protrusion within the interior of the "cup" defined by the resilient skirt. This is designed to fit within a recess provided in a hub within the valve assembly and prevents cocking of the valve member.

An advantage of the invention as applied to multiple sampling needles is that the one-way valve prevents chemical additives within the evacuated container from entering the bloodstream. If a tourniquet is removed or loosened before the intravenous needle is withdrawn from the vein, a pressure reverse could occur causing such backflow. The invention eliminates this risk.

According to a second embodiment of the invention, the blood sampling assembly includes a valve mounting structure upon which a specially designed valve member is seated. Both the mounting structure and valve are positioned within a chamber. The distal side of the valve member is adapted for proper seating upon the mounting structure. The proximal side of the valve member is flattened. The chamber is provided with a flat abutting surface which is designed to form a flush fit with the proximal side of the valve member.

The valve member utilized within the invention includes a resilient skirt extending from a main body member. It will accordingly have a cup-shaped appearance. In a preferred embodiment of the invention, the interior of the cup is flattened in the area of the main body member. In this manner, limited side-to-side movement is possible even when the valve is seated on the mounting structure. The value is accordingly self-centering to adjust for possible variations in the thickness of the resilient skirt.

Other objects and advantages of the invention will become apparent from the detailed description which follows.

BRIEF DESCRIPTION OF THE DRAWINGS

FIG. 1 is an exploded view of the invention.

FIG. 2 is a sectional elevation view of the invention.

FIG. 3 shows the invention after venipuncture and the application of an evacuated tube.

FIG. 4 shows the invention after withdrawal of the evacuated tube.

FIG. 5 is a cross-sectional view taken along lines 5—5 of FIG. 2.

FIG. 6 is an exploded perspective view of a second embodiment according to the invention.

FIG. 7 is a sectional view of the second embodiment according to the invention.

FIG. 8 is a sectional view which shows the operation of the second embodiment.

FIG. 9 is a sectional view of the second embodiment after removal of an evacuated tube.

FIG. 10 is a cross-sectional view taken along the plane of line 10—10 of FIG. 7.

FIG. 11 is an end view of a portion of the invention.

FIG. 12 is a sectional view of the portion of the invention shown in FIG. 11.

DESCRIPTION OF THE PREFERRED EMBODIMENT

Reference should be made to copending application Ser. No. 915,669 filed June 15, 1978, which concerns a blood sampling device having a check valve with a resilient skirt.

FIG. 1-5 illustrate the components of the valve assembly as applied to a multiple sampling needle assembly. A cup-shaped valve 10 is shown having resilient skirt 12 and inner protrusion 14. The protrusion 14 extends within slotted hole 32 of hub 22. The hole is defined by semi-cylindrical extensions 30 from the hub body, and ribs 28 provide support for the extensions. Hub 22 also includes threads 34 at its distal end to facilitate attachment of a holder 54.

Cannula 24 is attached to hub 22 by any suitable means, such as epoxy 26. Intravenous needle hub 20 is secured to hub 22 along interface 38 by conventional methods. The hub contains a cannula 16 attached by epoxy 18.

The hub 20 is constructed and valve 10 positioned such that a small chamber 36 is created between the intravenous side of the valve and the hub wall. Channel 42 establishes fluid communication between cannula 16 and chamber 36, as channel 46 does between slot 32 and cannula 24.

The hubs 20 and 22 may be constructed from any suitable material, and a polymer such as polystyrene is preferred. It is also advantageous to use a transparent or translucent material for at least the intravenous hub 20 so that the flow of blood may be easily observed.

FIGS. 3 and 4 illustrate the invention after the needle assembly has been threaded onto holder 54. An evacuated tube 58 is shown having elastomeric stopper 60. The tube is inserted within the holder 54.

The operation of the device shall now be described. After the needle assembly has been attached to the holder 54, the pointed tip 17 of cannula 16 is inserted into a patient's vein 56. To elevate the patient's blood pressure, a tourniquet has first been applied. The stopper 60 of evacuated tube 58 is penetrated by the pointed tip 25 of cannula 24. The negative pressure which develops after the tube has been positioned causes the skirt 12 of valve 10 to collapse. (See FIG. 3). The blood flows through cannula 16, channel 42, and will fill chamber 36. The flow will continue from the chamber 36, around valve 10, through slot 32, channel 44, cannula 24, and into tube 58. To prevent cocking of the valve 10 as a result of the pressure differential created and increased blood flow, the valve is provided with a center protrusion 14 which fits within slotted hole or recess 32. It has been found that the pressure at which the skirt collapses is dependent upon its physical structure and composition. The skirt is accordingly constructed to operate in response to the normal pressures associated with the sampling of blood.

After the tube is filled, it is removed from the apparatus. Skirt 12 will reassume its sealing position in relation to the walls of hub 20, thereby preventing further flow. (See FIG. 4). Additional evacuated tubes may be utilized to collect more samples without the need for additional venipunctures. The valve 10, normally closed even under tourniquet pressure (about 64 cm water head), prevents leakage while the tubes are exchanged. The valve is designed to remain closed under a 64 cm head for at least the time necessary for a user to conveniently exchange tubes. A multiple sampling device is thereby provided.

If the tourniquet is loosened before the cannula 16 has been withdrawn from the vein, a backflow condition can result due to the negative pressure created at IV needle point 17. To prevent blood and any chemicals present in tube 58 from entering the patient, backflow pressure will cause skirt 12 to expand against the walls of hub 20. As the reverse pressure becomes higher, the sealing force of the skirt becomes greater.

FIGS. 6–12 illustrate a second embodiment of the invention. It is similar to the first embodiment in a number of respects, but includes additional structure which provides several functional advantages.

FIG. 6 illustrates the blood sampling assembly 100 in an exploded view. Three members are shown: a first hub assembly 102, a second hub assembly 104 adapted for penetration of a vein, and an elastomeric cup-shaped valve 106 made from rubber or other suitable materials. Each hub assembly is made from plastic.

The valve member 106 includes a resilient skirt 108 which flares outwardly from the body portion 110 thereof at about 7° from the longitudinal axis of the assembly 100. The skirt 108 defines a cup-shaped valve portion. A protrusion 112 extends from the center of the body portion 110 towards the distal end of the assembly 100. The protrusion is relatively thick at its point of attachment to the body portion 110 and tapers to a rounded end 114. It is not only useful in the manner described in the first embodiment, but also facilitates handling in the assembly of the device. A number of such valves may be nested without sticking to each other. The distal side of the body portion 110 is provided with a flat annular surface 116 surrounding the protrusion. The outside diameter of the flat surface is defined by the inside surface of skirt portion 108.

The proximal side of the valve member 106 includes a flattened annular projection 118. The projection 118 is centrally positioned with respect to the body portion 110. It includes a flat surface 120 which is connected to the body portion by a tapering intermediate portion 122. The taper is approximately 20° with respect to the longitudinal axis of the assembly 100 in the embodiment shown.

By way of example to indicate the approximate size of the valve described herein, several representative dimensions are given. The valve member is about 0.156 inches in length as measured along the longitudinal axis of the assembly 100. This length will, of course, change slightly depending upon pressures exerted thereon. The maximum diameter of the skirt is about 0.194 inches. The thickest portion of the protrusion 112 has a diameter of 0.04 inches. The protrusion is approximately 0.06 inches in length. The projection 118 has a maximum diameter of 0.108 inches.

The first hub assembly 102, which is shown in greater detail in FIG. 7, includes means for mounting the valve member and is adapted for use with an evacuated blood collection container. Since this hub assembly is identical to hub assembly 22 described above, its structure will only be described briefly. The hub assembly 102 includes a pair of opposing semi-cylindrical extensions 124 defining a slotted hole 126 therebetween. The end portions of each of the extensions are beveled. Ribs 128 provide support for the extensions. A cannula 130 is provided within a bore 132 of suitable diameter at the distal end of the assembly 102. It is secured therein by conventional means such as epoxy 134. The slotted hole 126 is connected to the interior of the cannula by passage 136. The exterior surface of the assembly 102 includes threads 138 to allow the simple attachment of a tube holder.

The second hub assembly 104 is designed to mate with the first hub assembly, and may be welded or glued thereto along interface 140. A cannula 142 is provided within a bore 144 at the proximal end thereof. The distal end of the hub assembly 104 includes substantially cylindrical walls 146. These walls 146 and the interior walls 148 of the hub assembly define a valve chamber 150. The interior of the intravenous cannula 142 is connected to the valve chamber by means of passage 152.

A plurality of substantially T-shaped valve positioning members 154 extend from the walls 146, 148 of the second hub assembly into the valve chamber 150. They are shown most clearly in FIGS. 11 and 12. The valve positioning members have planar distal surfaces 156 which, after assembly of the two hub assemblies, are capable of interengaging the flattened annular projection 118 of the valve member 106. Flush contact may accordingly be made, particularly if potential backflow conditions exist which would tend to force the valve proximally within the valve chamber. It is apparent from the structure shown that cocking of the valve will be effectively prevented by the provision of the valve positioning member. In normal operation, a small gap will exist between surfaces 156 and projection 118 to allow the valve member 106 to self-center.

To facilitate the flow of blood into the valve chamber, the valve positioning members are laterally enlarged only at the portions 158 which may contact the flat surface 120 of the valve member. Blood may thereby easily flow between the narrower portions of the positioning members until it contacts the valve member. FIG. 11 illustrates the shape of the positioning members most clearly, and shows the enlarged or laterally extending portions of the T-shaped members spaced symmetrically about the longitudinal axis of the chamber.

As explained above, the blood sampling assembly is formed by the joining of two hub assemblies 102 and 104. It has been found that the assembly process is simplified by first positioning the valve member over a semi-cylindrical extensions and then joining the hub assemblies. To allow self-centering, the valve member is provided with a flat annular distal surface 116 which is slightly larger than the flat upper beveled surfaces of the semi-cylindrical extensions 124. Limited side-to-side movement is permitted, and the valve will center itself under flow conditions for optimal performance. This is advangageous as there may be slight variations in the thickness of the rubber valve skirt which could result in an improper seal with the chamber walls.

The operation of the blood sampling assembly shown in FIGS. 6-12 is similar to that of the assembly shown in FIGS. 1-5. A holder 160 is secured to the threaded portion 138 of the first hub assembly. The intravenous cannula 142 penetrates a vein, and blood flows through the cannula 142, the passage 152, and into the valve chamber 150. The valve member is constructed such that blood does not pass therethrough under venous pressure, even if a tourniquet has been utilized. A porous member may be provided within the valve to facilitate the passage of air from valve chamber 150.

Once a vein is found to be punctured, an evacuated tube 162 having a resilient stopper 164 is inserted within the holder. The stopper is pierced by cannula 130 as shown in FIG. 8. Under this large pressure differential, the skirt of the valve member collapses to allow the flow of blood into the slotted hole 126, through passage 136, through the cannula 130, and into the collection tube. Once filled, the tube is removed from the holder. If backflow conditions exist at any point in the procedure, the skirt of the cup-shaped valve member expands against the chamber walls 146 to prevent contamination of the patient. Movement of the valve member is restricted by the semi-cylindrical extensions and the valve positioning members 154. Proper operation is thereby insured at all times. It has been found that cocking is avoided even without the protrusion, but the latter feature is normally included for the manufacturing advantages noted above and its own ability to prevent cocking.

It will be appreciated that modifications can be made in either of the above-described structures without materially departing from the spirit of the invention. The scope of the invention should accordingly be determined by reference to the appended claims.

What is claimed is:

1. A multiple blood sampling assembly adapted to be coupled with an evacuated container to obtain blood samples from a patient, said assembly comprising:
    a. a housing having a forward end, a rear end, and having a chamber therein;
    b. a cannula mounted to the forward end of the housing, adapted for injection of a patient, and in fluid communication with the chamber;
    c. a valve mounting structure positioned within the chamber, said mounting structure having a recess therein; and
    d. a valve member mounted upon the mounting structure, said valve member having a resilient skirt in a normally sealing relation with the walls of the chamber, said skirt being capable of expanding against the chamber walls to prevent backflow towards the patient or collapsing to allow flow towards the rear end of the housing, and a protrusion extending towards the rear of the housing which is positioned within the recess in the mounting structure to prevent cocking of the valve.

2. An assembly as described in claim 1, wherein the valve member, skirt and protrusion are a one-piece elastomeric structure.

3. An assembly as described in claim 1 wherein the recess comprises a slotted hole defined by the mounting structure which includes two semi-cylindrical projections within the chamber.

4. An assembly as described in claim 1 wherein the housing includes means for attaching a holder for an evacuated container.

5. An assembly as described in claim 4 wherein the means for attaching a holder is a screw thread.

6. An assembly as described in claim 4 further including in combination a holder attached to the housing.

7. An assembly as described in claim 5 further including in combination an evacuated tube within said holder.

8. An assembly as described in claim 1 wherein a second cannula is attached to the rear end of the housing, said second cannula adapted for penetration of an evacuated container and being in fluid communication with the chamber.

9. An assembly as described in claim 1 wherein the physical structure and composition of the resilient skirt is such that said skirt maintains a sealing relationship with the chamber walls to prevent the flow of blood towards the rear end of the housing under tourniquet pressure.

10. An assembly as described in claim 1 wherein valve positioning means extend from the chamber walls towards the side of the valve member nearest the front end of the housing, said valve positioning means having a surface adjacent to said valve member and capable of limiting the forward motion thereof.

11. An assembly as described in claim 10 wherein a gap exists between said valve positioning means and said valve member.

12. An assembly as described in claim 10 or claim 11 wherein the front side of said valve member includes a planar surface and the surface of said valve positioning means adjacent said valve member is also planar.

13. An assembly as described in claim 12 wherein said valve positioning means includes a plurality of substantially T-shaped members extending from said chamber walls, said members extending rearwardly into said chamber towards said valve member, and the laterally extending portions of the T-shaped members being positioned adjacent said valve member.

14. An assembly as described in claim 3 wherein said valve member includes a body portion, the resilient skirt extending rearwardly from said body portion, said body portion including a substantially flat annular rear surface which rests upon said semi-cylindrical members, the width of said flat annular surface being greater than the width of said semi-cylindrical members such that said valve member is capable of limited lateral movement.

15. A multiple blood sampling assembly adapted to be coupled with an evacuated container to obtain blood samples from a patient, comprising:
 a housing having a forward end, a rear end, and having a chamber including substantially cylindrical side walls therein;
 a cannula mounted to the forward end of the housing which is adapted for penetration of a vein, said cannula being in fluid communication with said chamber;
 a valve mounting structure positioned within said chamber and extending towards the forward end of the housing;
 a valve member mounted upon said valve mounting structure, said valve member including a body portion and a skirt extending rearwardly from said body portion, said skirt normally contacting the cylindrical walls of said chamber, said valve mounting structure extending within said skirt so as to contact a rear surface of said body portion of said valve member; and
 valve positioning means extending rearwardly into said chamber from said housing, said valve positioning means having a rearward end adjacent the body portion of said valve member to limit the possible forward motion thereof, said valve mounting structure including a recess, said body portion of said valve member includes a rearwardly extending protrusion, said protrusion being positioned within said recess.

16. An assembly as described in claim 15 wherein said body portion of said valve member includes a flattened forward surface, said valve positioning means includes a flat rearward surface, the flattened forward surface of said valve member opposing the flat rearward surface of said valve positioning means.

17. An assembly as described in claim 15 wherein the recess is in the form of a slotted hole defined by two semi-cylindrical projections of the valve mounting structure.

18. An assembly as described in claim 17 wherein said body portion of said valve member includes a substantially flat annular rear surface which rests upon said semi-cylindrical members, the width of said flat annular surface being greater than the width of said semi-cylindrical members such that said valve is capable of limited lateral movement.

19. An assembly as described in claim 15 wherein said valve member is an integral elastomeric structure.

20. An assembly as described in claim 16 wherein said valve positioning means includes a plurality of substantially T-shaped members connected to the cylindrical side walls of said chamber, the laterally extending portions of the T-shaped members being opposite the points of connection to the side walls and spaced around the longitudinal axis of said chamber, said laterally extending portions including a flat rearward surface in opposed relation to the flattened forward surface of said valve member.

21. An assembly as described in claim 15 wherein a second cannula is attached to the rear end of the housing, said second cannula being in fluid communication with said chamber.

22. An assembly as described in claim 15 wherein said valve member is mounted on said valve mounting structure such that it is capable of limited lateral movement thereon, and there being a small gap between the valve member and the valve positioning means.

* * * * *